United States Patent
Kasugai

(10) Patent No.: US 8,080,996 B2
(45) Date of Patent: Dec. 20, 2011

(54) MAGNETIC RESONANCE IMAGING APPARATUS AND POSITION SETTING SUPPORT METHOD THEREOF

(75) Inventor: Takao Kasugai, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 456 days.

(21) Appl. No.: 12/346,096

(22) Filed: Dec. 30, 2008

(65) Prior Publication Data

US 2009/0182221 A1      Jul. 16, 2009

(30) Foreign Application Priority Data

Jan. 11, 2008      (JP) ................................. 2008-004473

(51) Int. Cl.
    *G01V 3/00*       (2006.01)
(52) U.S. Cl. ........................................ 324/307; 324/309
(58) Field of Classification Search .......... 324/300–322; 600/407–445
    See application file for complete search history.

(56) References Cited

U.S. PATENT DOCUMENTS

| | | | | |
|---|---|---|---|---|
| 5,446,548 | A | * | 8/1995 | Gerig et al. .................. 356/620 |
| 5,558,091 | A | * | 9/1996 | Acker et al. .................. 600/424 |
| 5,820,553 | A | * | 10/1998 | Hughes .......................... 600/426 |
| 5,823,192 | A | * | 10/1998 | Kalend et al. ................. 128/845 |
| 7,343,189 | B2 | * | 3/2008 | Kagermeier et al. ......... 600/407 |
| 2009/0245607 | A1 | * | 10/2009 | Sugiura ......................... 382/131 |
| 2011/0034209 | A1 | * | 2/2011 | Rubinsky et al. .......... 455/556.1 |

FOREIGN PATENT DOCUMENTS

| | | |
|---|---|---|
| JP | 10-127596 | 5/1998 |
| JP | 10-258064 | 9/1998 |
| JP | 2002-102203 | 4/2002 |
| JP | 2006-167042 | 6/2006 |

* cited by examiner

*Primary Examiner* — Brij B Shrivastav
(74) *Attorney, Agent, or Firm* — Oblon, Spivak, McClelland, Maier & Neustadt, L.L.P.

(57) ABSTRACT

According to the present invention, in a magnetic resonance imaging apparatus that receives magnetic resonance signals emitted from a patient by using a reception coil and reconstructs an image of the test subject from the received magnetic resonance signals, first and second cameras image positions of the patient and the reception coil and an audio recorder records the same to be stored in a PACS server when setting the reception coil. Further, when setting the reception coil for a subsequent time, information of the positions of the test subject and the reception coil is read from the PACS server and confirmed by using a monitor and a speaker.

20 Claims, 8 Drawing Sheets

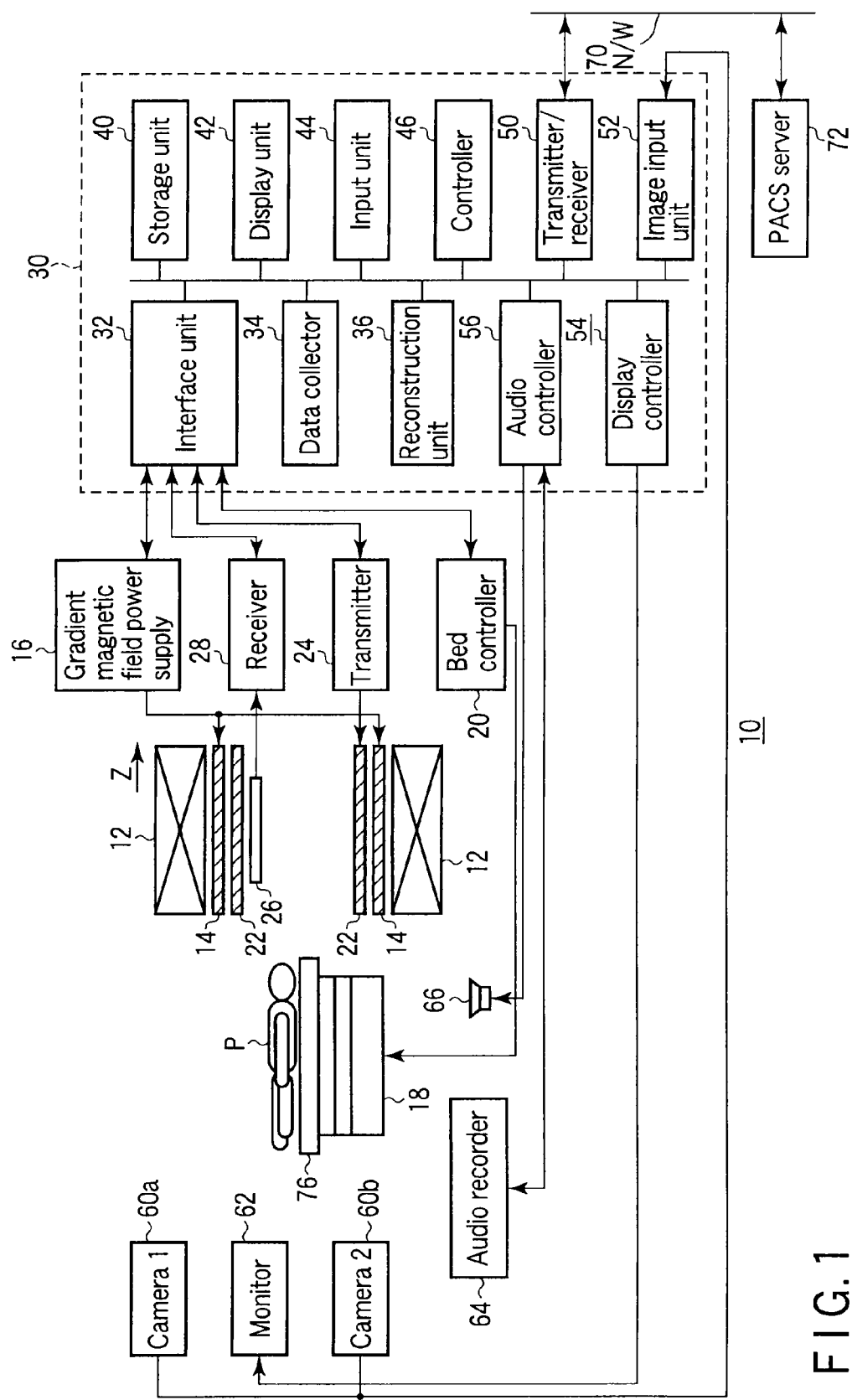
F I G. 1

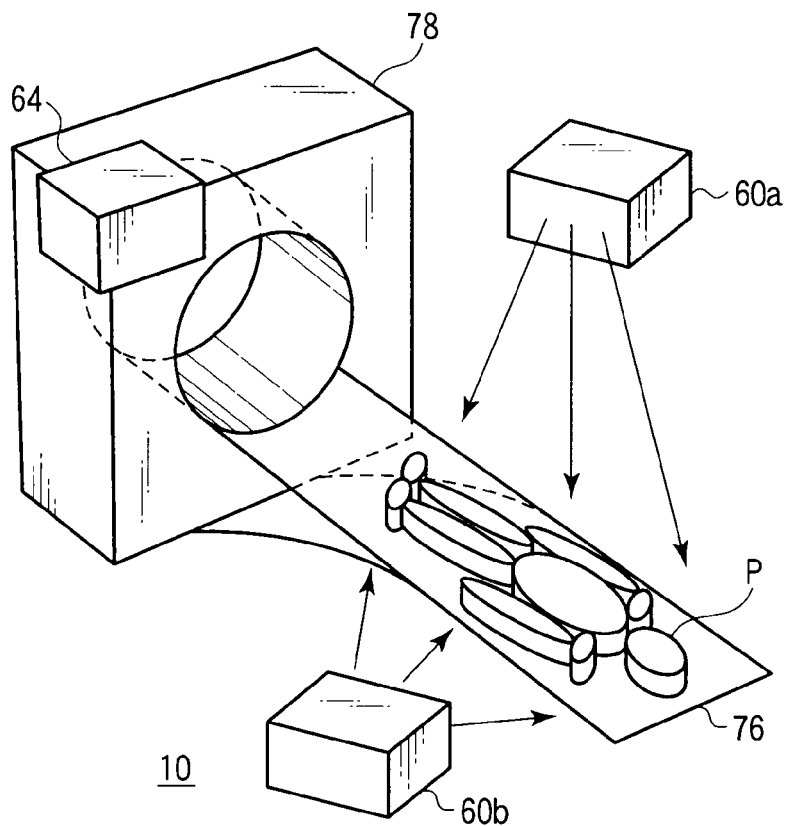
F I G. 2A
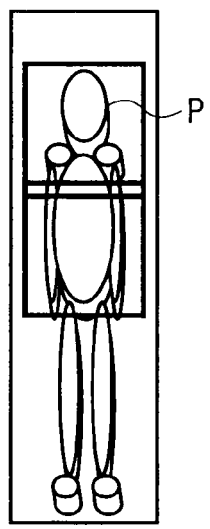
F I G. 2B
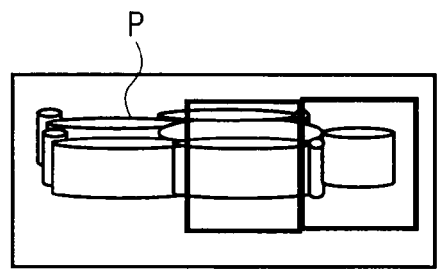
F I G. 2C

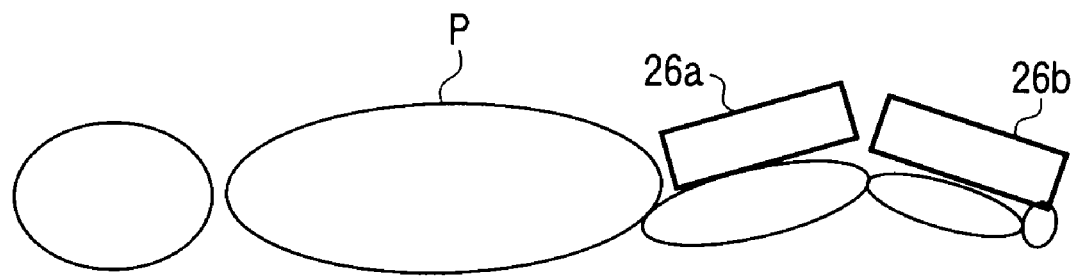
F I G. 6A
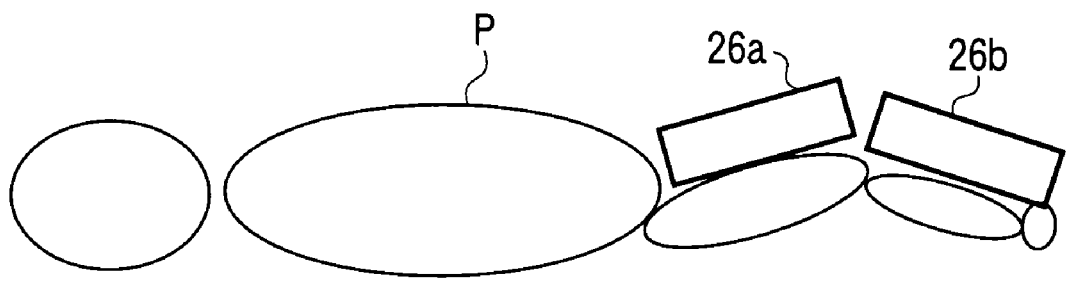
F I G. 6B

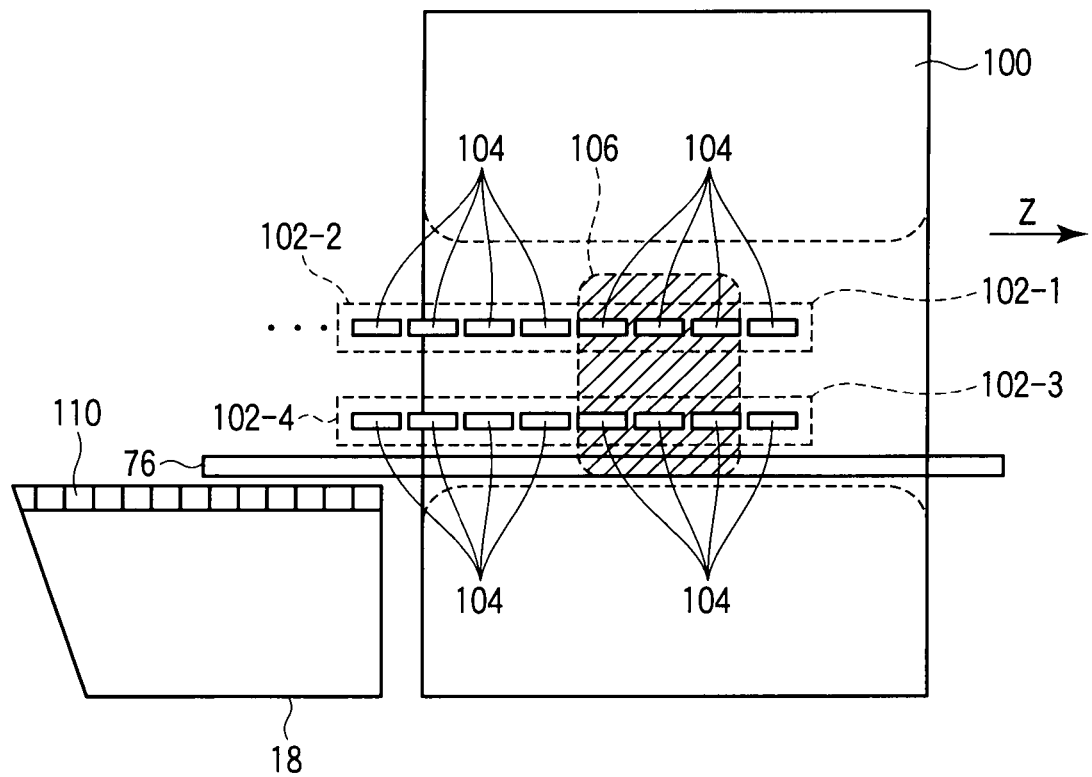
F I G. 8
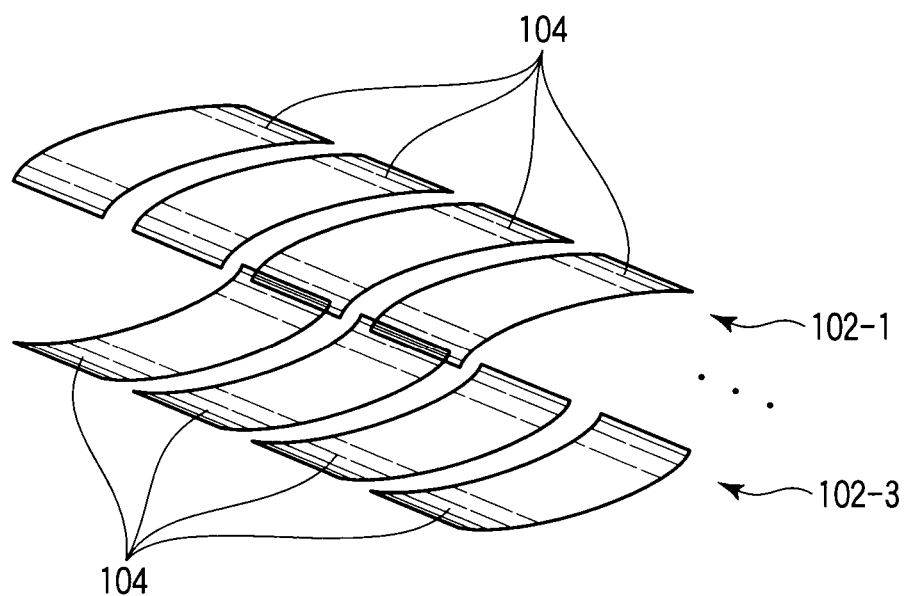
F I G. 9

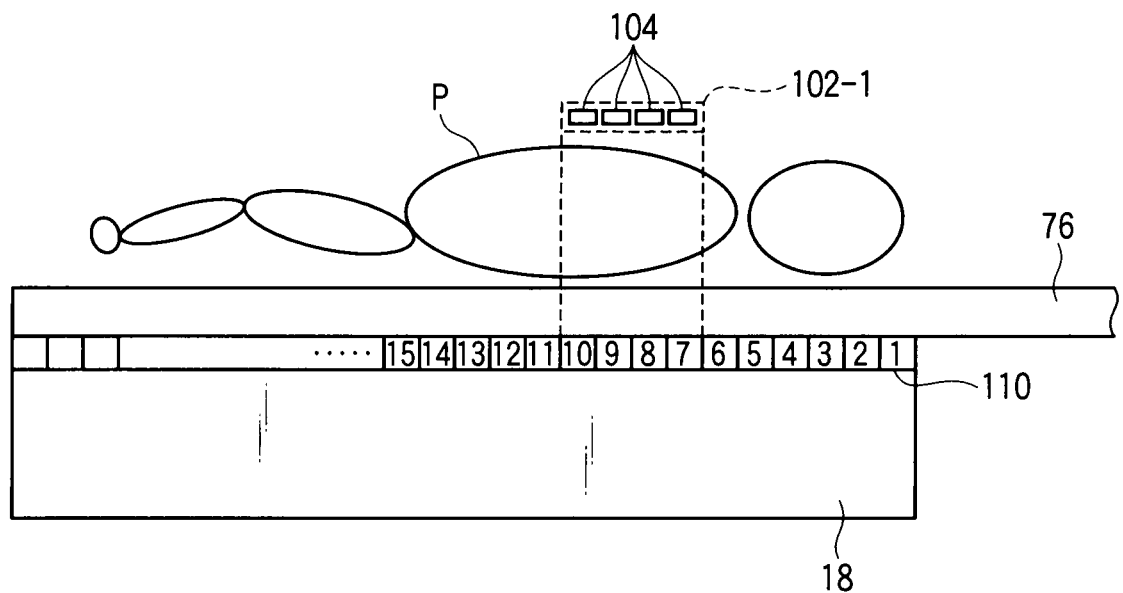
F I G. 10
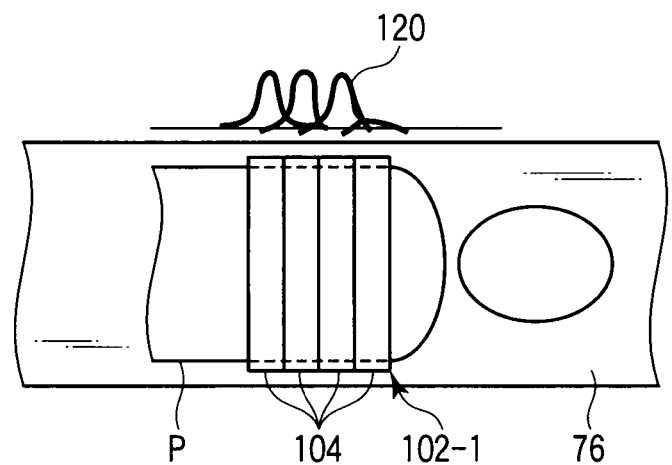
F I G. 11

MAGNETIC RESONANCE IMAGING APPARATUS AND POSITION SETTING SUPPORT METHOD THEREOF

CROSS-REFERENCE TO RELATED APPLICATIONS

This application is based upon and claims the benefit of priority from prior Japanese Patent Application No. 2008-004473, filed Jan. 11, 2008, the entire contents of which are incorporated herein by reference.

BACKGROUND OF THE INVENTION

1. Field of the Invention

The present invention relates to a magnetic resonance imaging apparatus as a medical diagnostic device and a position setting support method thereof, and more particularly to a magnetic resonance imaging apparatus which is used when, e.g., reception coils should be more accurately set and stores patient information in, especially, a medical picture archiving and communication system (PACS) through a network.

2. Description of the Related Art

In recent years, when examining a patient (a test subject), imaging an imaging target region of the same patient under the same imaging conditions as before and after an operation or follow-up is often desired in a magnetic resonance imaging apparatus.

Further, in regard to a medical diagnostic imaging apparatus, for example, Jpn. Pat. Appln. KOKAI Publication No. 10-258064 discloses an apparatus that positions and fixes a head region of a test subject. Furthermore, Jpn. Pat. Appln. KOKAI Publication No. 2006-167042 discloses an apparatus that simultaneously displays a comparison image based on a recorded image acquired from a past examination and a scan image acquired from a current examination in an overlapping manner and obtains an image at a position substantially the same as that in the past examination in accordance with matching of display positions of these images.

However, in the apparatus disclosed in Jpn. Pat. Appln. KOKAI Publication No. 10-258064, since a region examined by the diagnostic imaging apparatus is not restricted to a head region, it is considered that condition matching means having higher general versatility is required. Moreover, providing such an apparatus leads to increase in cost, and there is also a concern about a burden imposed on a test subject whose head region is forcibly fixed during an examination. Additionally, since a time to fix a head region is required, an examination time may become long. Further, although a test subject is fixed by using, e.g., a fixing band, an imaging cloth, or a net, this imposes a considerable burden on the patient.

Furthermore, in the apparatus disclosed in Jpn. Pat. Appln. KOKAI Publication No. 2006-167042, there is no description about setting reception coils such as a magnetic resonance imaging apparatus.

In case of the magnetic resonance imaging apparatus, an image may become completely different depending on how reception coils are set even though imaging is carried out under the same conditions. Therefore, a method of recording, e.g., coil names or coil positional information in a previous examination is adopted.

However, even if such a method is adopted, there is no method that is suitable for recording a relative position relationship between reception coils and a test subject that is the biggest problem, and a countermeasure must be taken.

BRIEF SUMMARY OF THE INVENTION

Therefore, it is an object of the present invention to provide a magnetic resonance imaging apparatus that can easily carry out imaging conditions or setting information for subsequent imaging which are equal to imaging conditions or setting information for a previous imaging at the time of performing imaging more than once and to provide a position setting support method thereof.

That is, an object of the present invention is to provide a magnetic resonance imaging apparatus that receives magnetic resonance signals emitted from a test subject by using a reception coil and reconstructs an image of the test subject from the received magnetic resonance signals, comprising:

a storage unit that stores positions of the test subject and the reception coil when setting the reception coil; and a notification unit that reads and notifies the positions of the test subject and the reception coil stored in the storage unit to confirm the positions of the test subject and the reception coil in a previous time when setting the reception coil for a subsequent time.

Furthermore, another object of the present invention is to provide a magnetic resonance imaging apparatus that receives magnetic resonance signals emitted from a test subject laid on a bed by using a reception coil in which a plurality of element coils are aligned and reconstructs an image of the test subject from the received magnetic resonance signals, comprising:

a calculation unit that calculates set positions of the plurality of element coils based on each projection data in an alignment direction of the plurality of element coils based on the plurality of magnetic resonance signals received by the plurality of element coils, respectively;

a storage unit that stores positions of the test subject and the plurality of element coils calculated by the calculation unit when setting the plurality of element coils; and a notification unit that reads and notifies the positions of the test subject and the element coils stored in the storage unit to confirm the positions of the test subject and the element coils in a previous time when setting the plurality of element coils for a subsequent time.

Moreover, still another object of the present invention is to provide a position setting support method of a magnetic resonance imaging apparatus that receives magnetic resonance signals emitted from a test subject by using a reception coil and reconstructs an image of the subject from the received magnetic resonance signals, comprising:

previously setting a position of the test subject and positions of the test subject and the reception coil prior to an examination;

recording information indicative of the position of the test subject and the positions of the test subject and the reception coil set at the previously setting;

performing an examination by using the magnetic resonance imaging apparatus;

reading the information indicative of the position of the test subject and the positions of the test subject and the reception coil recorded at the recording before again performing an examination after the examination;

setting a position of the test subject and positions of the test subject and the reception coil at the present time based on the information indicative of the position of the test subject and the positions of the test subject and the reception coil read at the reading the information indicative of the position of the reception coil; and again performing an examination by using the magnetic resonance imaging apparatus at the position of the test subject and the positions of the test subject and the reception coil set at the setting the positions.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a structure of a magnetic resonance imaging apparatus according to a first embodiment of the present invention;

FIGS. 2A to 2C are views for explaining installation of first and second cameras and an audio recorder in the magnetic resonance imaging apparatus according to the first embodiment of the present invention;

FIGS. 6A and 6B are views for explaining body positions of the patient and setting of the reception coils and also explaining examples of the setting that remains unchanged in the previous examination and the current examination based on the first embodiment;

FIG. 8 is a view showing an attachment example of reception coil units in an MRI apparatus according to a third embodiment of the present invention;

FIG. 9 is a perspective view showing an alignment situation of element coils 104 in reception coil units 102-1 to 102-3;

FIG. 10 is a view showing a relationship between the element coils 104 attached to a test subject P and a marker of a bed 18; and FIG. 11 is a view for explaining the element coils 104 attached to the test subject P and projection data based on magnetic resonance signals 120 received by the element coils 104 placed in an imaging utilization range 106.

DETAILED DESCRIPTION OF THE INVENTION

Figure 3:
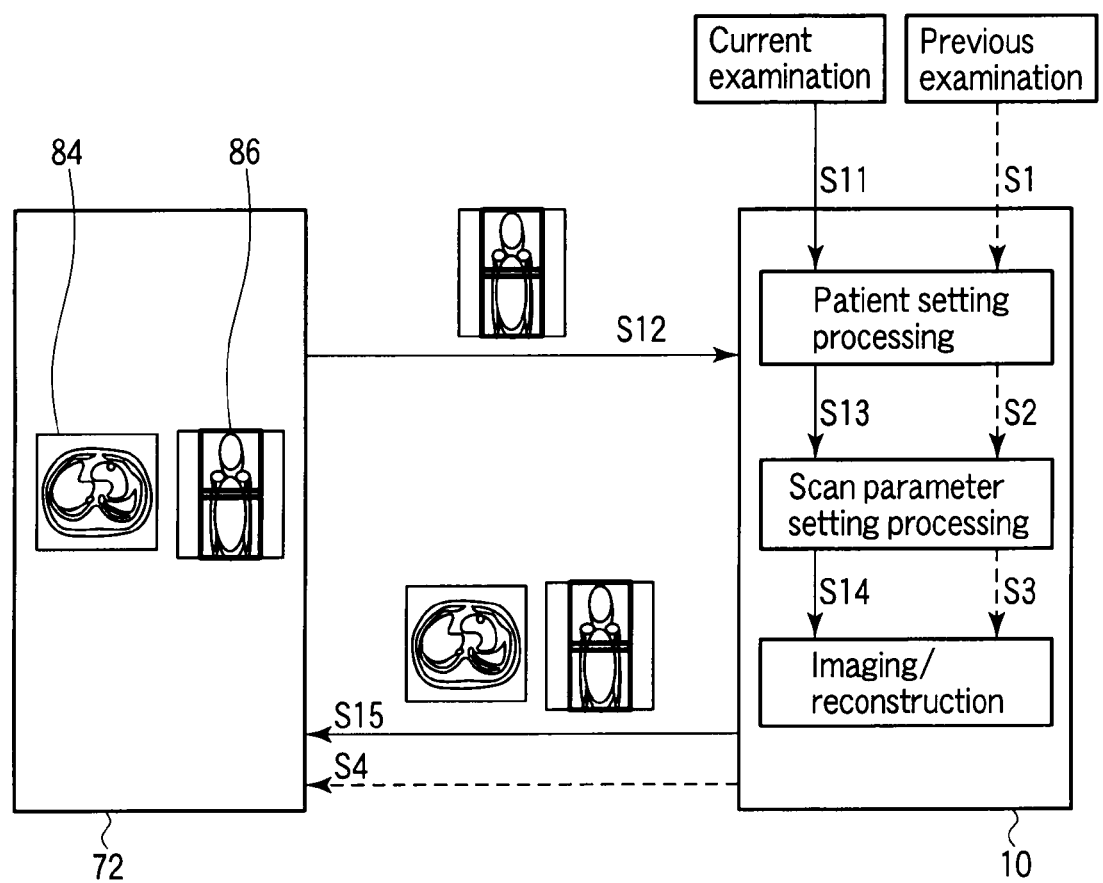
FIG. 3 is a flowchart for explaining an operation of the magnetic resonance imaging apparatus according to the first embodiment of the present invention.

Embodiments according to the present invention will now be explained hereinafter with reference to the drawings.

First Embodiment

FIG. 1 is a block diagram showing a system configuration of a magnetic resonance imaging (MRI) apparatus hereinafter according to a first embodiment of the present invention.

In FIG. 1, an MRI apparatus 10 in this embodiment is constituted of a magnetostatic field magnet 12, a gradient magnetic field coil 14, a gradient magnetic field power supply 16, a bed 18, a bed controller 20, a transmission coil 22, a transmitter 24, a reception coil 26, a receiver 28, a computer system 30, a first camera (depicted as camera 1 in the drawing) 60a, a second camera (depicted as camera 2 in the drawing) 60b, a monitor 62, an audio recorder 64, and a speaker (SP) 66.

The magnetostatic field magnet 12 has a hollow cylindrical shape and generates a uniform magnetostatic field in its inner space. As this magnetostatic field magnet 12, for example, a permanent magnet or a superconducting magnet is used.

The gradient magnetic field coil 14 has a hollow cylindrical shape and is arranged in the magnetostatic field magnet 12. The gradient magnetic field coil 14 is formed by combining three types of coils associated with respective axes X, Y, and Z orthogonal to each other. Further, the three coils in the gradient magnetic field coil 14 individually receive supply of a current from the gradient magnetic field power supply 16, thereby generating gradient magnetic fields whose magnetic field intensities vary along the respective axes X, Y, and Z. It should be noted that a direction of the Z-axis is the same as, e.g., a direction of a magnetostatic field.

The gradient magnetic fields of the respective axes X, Y, and Z correspond to, e.g., a slice selection gradient magnetic field Gs, a phase encoding gradient magnetic field Ge, and a readout gradient magnetic field Gr, respectively. The slice selection gradient magnetic field Gs is utilized to arbitrarily determine an imaging cross section. The phase encoding gradient magnetic field Ge is utilized to change a phase of a magnetic resonance signal in accordance with a spatial position. The readout gradient magnetic field Gr is utilized to change a frequency of a magnetic resonance signal in accordance with a spatial position.

A patient P is laid down on a top panel 76 of the bed 18. The patient P is laid down on the top panel 76 of the bed 18 to be carried into a cavity (an imaging opening) of the gradient magnetic field coil 14. The top panel 76 of the bed 18 is driven by the bed controller 20 and moved in a longitudinal direction and a vertical direction thereof. Usually, the bed 18 is installed in such a manner that this longitudinal direction becomes parallel to a central axis of the magnetostatic field magnet 12.

The transmission coil 22 is formed by accommodating one or more coils in a cylindrical case and arranged in the gradient magnetic field coil 14. This transmission coil 22 receives a radio-frequency pulse from the transmitter 24 to generate a high-frequency magnetic field.

The transmitter 24 includes an oscillator, a phase selector, a frequency converter, an amplitude modulator, a radio-frequency power amplifier, and others. The oscillator generates a radio-frequency signal having a resonance frequency inherent to a target atomic nucleus in a magnetostatic field. The phase selector selects a phase of the radio-frequency signal. The frequency converter converts a frequency of a radio-frequency signal output from the phase selector. The amplitude modulator modulates an amplitude of a radio-frequency signal output from the frequency modulator in accordance with, e.g., a sync function. The radio-frequency power amplifier amplifies a radio-frequency signal output from the amplitude modulator. Furthermore, the transmitter 24 transmits a radio-frequency pulse corresponding to a Larmor frequency to the transmission coil 22 as a result of the operations of these units.

The reception coil 26 is mounted on the top panel 76, included in the top panel 76, or attached to the test subject P, and it is arranged in the gradient magnetic field coil 14. The reception coil 26 receives each magnetic resonance signal emitted from the patient P due to an influence of the radio-frequency magnetic field. An output signal from the reception coil 26 is input to the receiver 28. The receiver 28 generates magnetic resonance signal data based on an output signal from the reception coil 26.

The computer system 30 is constituted of an interface unit 32, a data collector 34, a reconstruction unit 36, a storage unit 40, a display unit 42, an input unit 44, a controller 46, a transmitter/receiver 50, an image input unit 52, a display controller 54, and an audio controller 56.

To the interface unit 32 are connected with the gradient magnetic field power supply 16, the bed controller 20, the transmitter 24, the reception coil 26, the receiver 28, and others. The interface unit 22 inputs/outputs signals transmitted/received between the respective connected units and the computer system 30.

The data collector 34 collects digital signals output from the receiver 28 through the interface unit 32. The digital signals collected by this data collector 34, i.e., magnetic resonance signal data is stored in the storage unit 40. The reconstruction unit 36 executes post-processing, i.e., reconstruction such as Fourier transformation with respect to the magnetic resonance signal data stored in the storage unit 40 to obtain spectrum data of a desired nuclear spin or image data in the patient P.

The storage unit 40 stores the magnetic resonance signal data and the spectrum data or the image data in accordance with each patient. The display unit 42 displays various kinds of information, e.g., the spectrum data or the image data under control of the controller 46. As the display unit 42, a display device such as a liquid crystal display can be utilized.

The input unit 44 accepts various kinds of commands or information input from an operator. As the input unit 44, a pointing device such as a mouse or a track ball, a selection device such as a mode changeover switch, or an input device such as a keyboard can be appropriately used. The controller 46 is formed of a non-illustrated CPU and memories, and collectively controls the MRI apparatus according to this embodiment. The controller 46 has a control function that realizes known functions in the MRI apparatus 10.

The transmitter/receiver 50 is an interface that transmits/receives data between this MRI apparatus 10 and a later-explained medical picture archiving and communication system (PACS) 72 through a network (N/W) 70.

The image input unit 52 inputs images input from the first and second cameras 60a and 60b as image data. The display controller 54 outputs an image recorded in the later-explained PACS 72 to the monitor 62 through the network 70. The audio controller 56 inputs audio recorded by the audio recorder 64 as audio data and outputs the audio data recorded in the PACS 72 to the speaker 66.

For example, as shown in FIG. 2A, the first and second cameras 60a and 60b perform imaging to store a body position of the patient P and setting information of the reception coil 26. In regard to installation positions of the first camera 60a and the second camera 60b, these cameras are installed at positions where the patient is visually confirmed from the upper side as shown in FIG. 2B or they are installed at positions where the patient P is visually confirmed in a lateral direction as shown in FIG. 2C to clarify a body position of the patient P and set positions of the reception coil 26, for example.

The audio recorder 64 is also provided to store a body position of the patient P and setting information of the reception coil 26 like the first and second cameras 60a and 60b. However, an installation position thereof is not specified.

The monitor 62 and the speaker 66 are provided to confirm a body position of the patient P and a set position of each reception coil 26 acquired by the first and second cameras 60a and 60b in the past, and use image and audio for confirmation. Moreover, although installation positions of these members are not depicted, it is preferable to provide these members in a shield. Here, installation in the shield means, e.g., a state where the monitor 62 and the speaker 66 are provided on a pedestal 78 or a state where they are provided on a wall of a room in which the bed 18 is installed. That is because, even though an operator can use the monitor 62 or the speaker 66 to confirm a body position of the patient P or a set position of each reception coil 26, the operator must enter/leave the shield every time a body position of the patient P and setting of each reception coil 26 are confirmed if the monitor 62 and the speaker 66 are provided outside the shield, which is troublesome.

The PACS 72 is storing means for storing images acquired by the first and second cameras 60a and 60b, a body position of the patient P, a set position of each reception coil 26, information of the patient, and others.

An operation of the thus configured MRI apparatus 10 will now be explained with reference to a flowchart of FIG. 3.

It should be noted that an operation required to image the patient P is the same as that performed in a conventionally utilized MRI apparatus, thereby omitting a detailed explanation thereof.

First, in case of an MRI examination (a previous examination) conducted for the first time for the patient, an operator sets a body position of the patient P and each reception coil 26 by patient setting processing based on an appropriate method in step S1. Here, the first and second cameras 60a and 60b perform imaging, and the audio recorder 64 stores audio. Moreover, optimum scan parameters are set by scan parameter setting processing in step S2. Then, in step S3, an imaging sequence and reconstruction are effected by the MRI apparatus 10.

When the imaging sequence is completed, an image acquired by the operator is transferred to be stored in the PACS server 72. Here, an acquired image (an examination image 84), image data of a body position of the patient P (a direction on the top panel 76) and a set position of each reception coil 26 acquired by the first and second cameras 60a and 60b, audio data concerning imaging (a patient, coil setting information, scan parameter information 86, and others) recorded by the audio recorder 64 are transferred to the PACS server 72 to be stored.

Subsequently, when the same examination as that in the previous time is carried out with respect to the patient P, scan plan processing is performed in step S11. Then, set images concerning a body position of the patient and a set position of each reception coil 26 in a previous examination are acquired from the PACS server 72 to be displayed on the monitor 62 through the display controller 54 in step S12. Additionally, audio data concerning imaging is converted so that audio is generated from the speaker 66 via the audio controller 56.

Figure 4A:
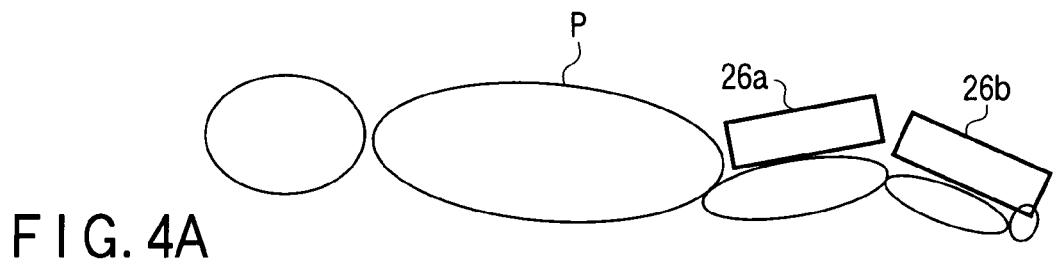
FIGS. 4A and 4B are views for explaining body positions of a patient and setting of reception coils and also explaining examples of the body position that differs in a previous examination and a current examination.
Figure 4B:
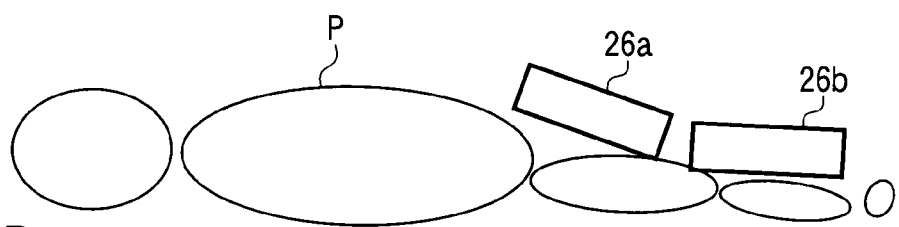
Figures 5A, 5B:
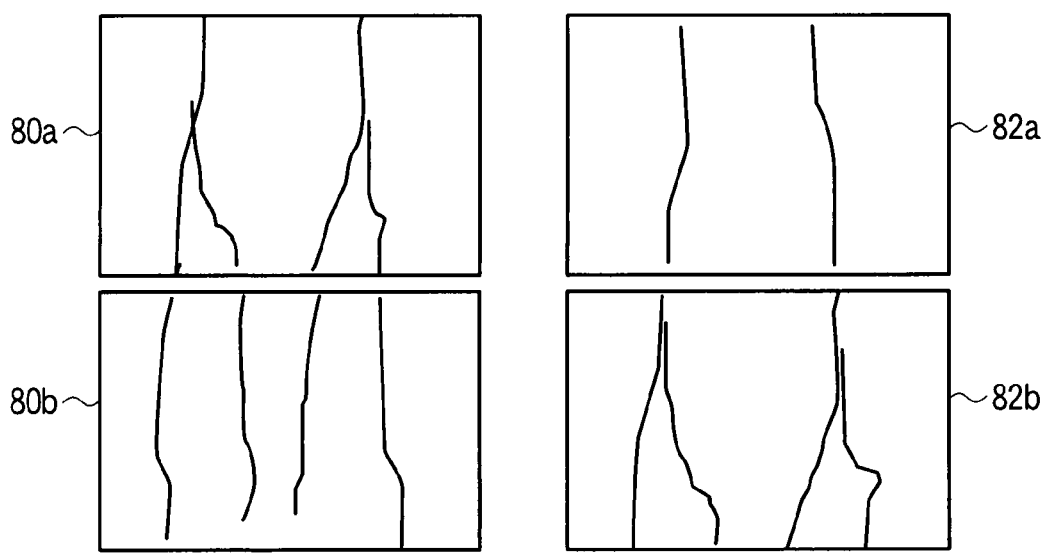
FIGS. 5A and 5B are views for explaining the body positions of the patient and setting of the reception coils and also explaining examples of acquired images when the body position differs in the previous examination and the current examination.

For example, it is assumed that the patient P adopts a body position that he/she slightly bends his/her knees and reception coils 26a and 26b are set in the previous examination as shown in FIG. 4A. It should be noted that the reception coils 26a and 26b correspond to the reception coil 26 in this case. On the other hand, it is assumed that the patient P adopts a body position that he/she straightens his/her knees and the reception coils 26a and 26b are set in the current examination as shown in FIG. 4B. Then, acquired images in the previous examination are such images 80a and 80b as depicted in FIG. 5A, whereas acquired images in the current examination are such images 82*a* and 82*b* as shown in FIG. 5B, and the images in the current and previous examinations are greatly different from each other.

Thus, when acquired images and audio data stored at the time of the previous examination are read from the PACS server 72, converted, and then output to the monitor 62 and the speaker 66, a body position of the patient P and set positions of the reception coils 26 (26*a* and 26*b*) in the previous examination can be confirmed.

For example, it is assumed that the patient P adopts a body position that he/she slightly bends his/her knees and the reception coils 26*a* and 26*b* are set in the previous examination as shown in FIG. 6A. Here, the operator confirms whether the examination of the patient P has been carried out. If the examination has been carried out, a body position of the patient P, set position of the reception coils 26 (26*a* and 26*b*), and others in that examination are read from the PACS server 72.

Additionally, in step S13, positioning processing is effected. That is, the operator sets a body position of the patient P and the reception coils 26*a* and 26*b* for the current examination as shown in FIG. 6B while confirming the body position of the patient P and the reception coils 26 (26*a* and 26*b*) read from the PACS 72 by using the monitor 62 or the speaker 66. Further, information of the body position of the patient P and the reception coils 26 (26*a* and 26*b*) at this time is also again acquired by the first and second cameras 60*a* and 60*b* and the audio recorder 64.

Thereafter, in step S14, imaging and reconstruction for the current examination are performed. Then, in step S15, image data, audio data, and others of a body position of the patient P and set positions of the reception coils 26 acquired by the first and second cameras 60*a* and 60*b* and the audio recorder 64 are transferred together with images acquired by the MRI apparatus 10 to the PACS server 72 to be saved as in step S4.

As explained above, in the current examination, the settings of the patient P and the reception coils 26 (26*a* and 26*b*) are configured based on the information in the previous examination. Further, when processing operations in steps S11 to S15 are continuously and repeatedly performed to carry out the same examination every time after execution of steps S1 to S4 in the first examination, the same manipulations are effected.

As explained above, according to the first embodiment, the same settings of a body position of the patient and the reception coils as those in the previous examination can be configured, thus effecting the same imaging as that in the previous time.

Second Embodiment

A second embodiment according to the present invention will now be explained.

Although the example where the PACS server is utilized to save information and effect positioning has been explained in the first embodiment, the present invention is not restricted thereto. For example, when storing the above-explained information, the PACS server does not have to be necessarily used, and a local computer system or a medium for storage may be utilized.

It should be noted that a basic structure of an MRI apparatus in this second embodiment is the same as the structure of the MRI apparatus according to the first embodiment depicted in FIGS. 1 to 6 except that a local computer system 90 is connected in place of the PACS server 72 illustrated in FIG. 1 and the operation of the MRI apparatus is substantially the same as that in the first embodiment, and hence like reference numbers denote like parts to omit illustrations and explanations thereof, and different part alone will be explained.

Figure 7:
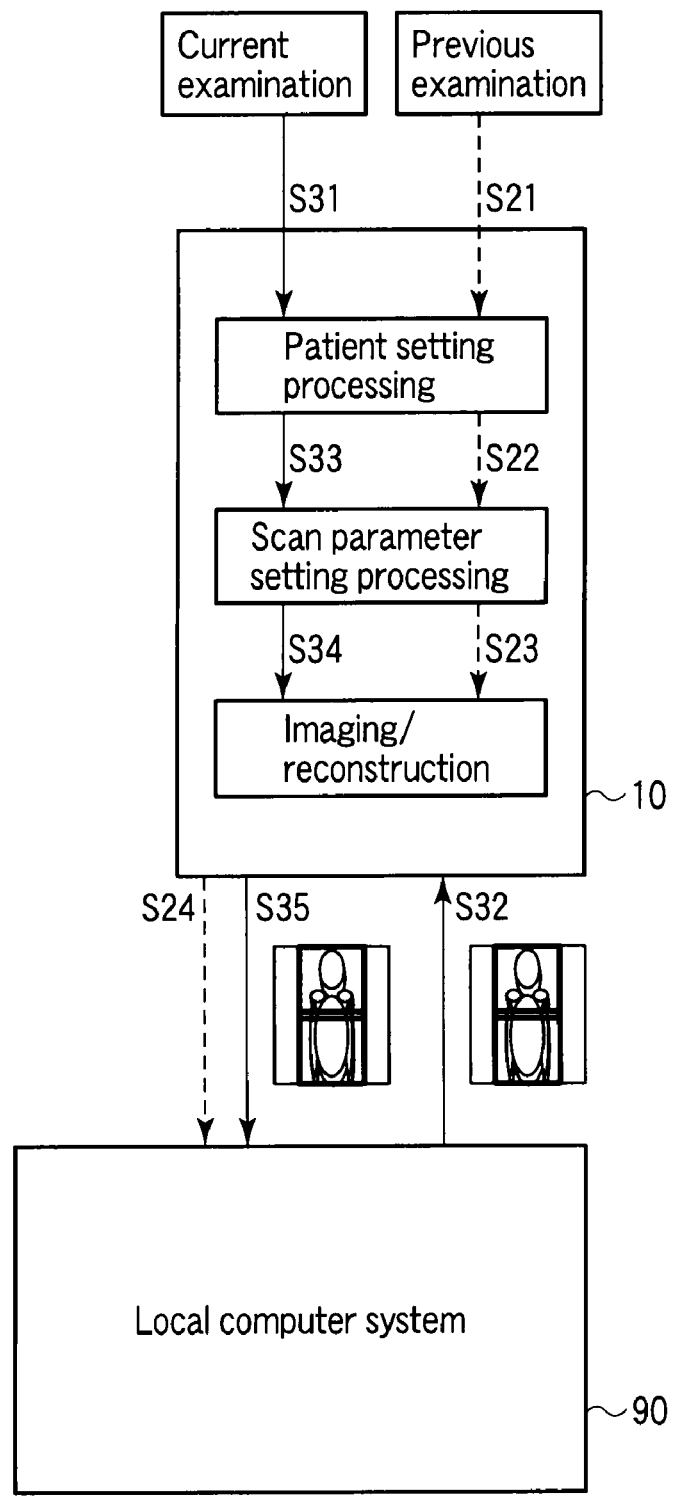
FIG. 7 is a flowchart for explaining an operation of a magnetic resonance imaging apparatus according to a second embodiment of the present invention.

An operation of the thus configured MRI apparatus 10 will now be explained with reference to a flowchart of FIG. 7.

First, in case of an MRI examination (a previous examination) performed for the first time for a patient, an operator sets a body position of a patient P and each reception coil 26 in accordance with a scan plane based on an appropriate method in step S21. Here, imaging performed by first and second cameras 30*a* and 30*b* and audio information (data) obtained by an audio recorder 64 are stored. Further, scan parameters are set based on scan parameter setting processing in step S22. Then, in step S23, the MRI apparatus 10 carries out an imaging sequence and reconstruction.

When the imaging sequence is completed in this manner, images and audio acquired and recorded by the operator are transferred in step S24. That is, image data, audio data, and others indicative of a position of the patient P and set positions of the reception coils 26 acquired by the first and second cameras 60*a* and 60*b* are transferred together with the acquired images to a local computer system 90.

Subsequently, when the current examination is the same as the previous examination for the patient P, scan plan processing is carried out in step S31. Then, in step S32, setting images indicative of a position of the patient P and set positions of the reception coils 26 in the previous examination are acquired from the local computer system 90 and displayed on a monitor 62.

Further, when positioning processing is executed in step S33, imaging and reconstruction for the current examination are performed in subsequent step S34. Then, in step S35, image data, audio data, and others indicative of a position of the patient P and set positions of the reception coils 26 acquired by the first and second cameras 60*a* and 60*b* and an audio recorder 64 are transferred together with images acquired by the MRI apparatus to the local computer system 90 as in step S24.

As explained above, according to the second embodiment, the same setting of a body position of the patient and the reception coils as that in the previous examination can be configured, thereby effecting the same imaging as that in the previous time.

It should be noted that the setting information and others indicative of a body position of the patient P and the reception coils 26 stored in the PACS server system 72 and the local computer system 90 are images acquired by the first and second cameras 60*a* and 60*b* and audio data recorded by the audio recorder 64 in the first and second embodiments, but either images or audio data can suffice as long as setting information and others indicative of a body position of the patient P and the reception coils 26 can be confirmed. Alternatively, any other means may be used as long as setting information and others indicative of a body position of the patient P and the reception coils 26 can be confirmed.

Further, as the information to be stored, it is possible to store not only the setting information indicative of a body position of the patient and the reception coils but also setting information of, e.g., an ECG sensor.

Third Embodiment

A third embodiment according to the present invention will now be explained.

Although setting information of a body position of the patient P and each reception coil is stored by using the first and second cameras 60*a* and 60*b* or the audio recorder 64 in the first and second embodiments, the present invention is not restricted thereto. In the third embodiment, a relative position of the patient P and each reception coil is obtained at the time of pre-scan before main scan.

FIG. 8 is a view showing an attachment example of reception coil units of an MRI apparatus according to a third embodiment of the present invention.

It should be noted that, since a basic structure of the MRI apparatus in this third embodiment is equal to the structure of the MRI apparatus according to the first embodiment depicted in FIGS. 1 to 6 except structures of each reception coil and the bed shown in FIG. 1 and its operation is also substantially equal, like reference numbers denote like parts to omit illustrations and explanations thereof, and different parts alone will be explained.

In the example depicted in FIG. 8, four reception coil units 102 are attached. It should be noted that, when these reception coil units 102 must be discriminated from each other, they are referred to as reception coil units 102-1, 102-2, 102-3, and 102-4, respectively.

The reception coil units 102-1 and 102-2 are abdominal coils and attached to a front surface side of a body of a test subject P. The reception coil units 102-3 and 102-4 are spinal coils, and they are mounted at arbitrary positions on a top panel 76 so that the test subject P lies face up thereon or they are attached to a back side of the test subject P to be mounted on the top panel 76 together with the test subject P. Therefore, mounting positions of these reception coil units 102 on the top panel 76 are indeterminate. As the reception coil unit 102, one optimized for each region, e.g., a knee may be used as well.

As shown in FIGS. 8 and 9, a plurality of (four in this example) of element coils 104 are aligned and formed in one direction at fixed intervals in each of the reception coil units 102-1, 102-2, 102-3, and 102-4. As shown in FIG. 8, each of the reception coil units 102-1, 102-2, 102-3, and 102-4 is used in a posture that an alignment direction of the element coils 104 coincides with a Z-axis direction. It should be noted that FIG. 9 is a perspective view showing an alignment situation of the element coils 104 in the reception coil units 102-1 and 102-3.

The reception coil units 102-1 and 102-2 may be individually disposed at arbitrary positions, or may be coupled with each other through a mechanical coupling mechanism to be disposed at fixed intervals. This can be likewise applied to the reception coil units 102-3 and 102-4.

The element coil 104 may be formed by further coupling a plurality of coils. There is also a scheme called Mode Matrix that a plurality of, e.g., three or four coils are re-coupled to be used.

Furthermore, reference number 100 in FIG. 8 denotes a pedestal accommodating a magnetostatic field magnet 12, a gradient magnetic field coil 14, and others. In an imaging space in the pedestal 100, an imaging utilization range actually used for imaging is only a part as denoted by reference number 106. The reception coil units 102-1, 102-2, 102-3, and 102-4 are larger than the imaging utilization range 106, and some of the element coils 104 alone can be placed in the imaging utilization range 106. In the example depicted in FIG. 8, the second to fourth element coils 104 in each of the reception coil units 102-1 and 102-3 are placed in the imaging utilization range 106. That is, in a state depicted in FIG. 8, the element coils 104 placed in the imaging utilization range 106 are used for actual imaging. Therefore, as realization of multichannel of array coils advances, it is required to know positions of the reception coil units or positions of the respective element coils 104 to appropriately select the element coils used for imaging.

Determination of positions of the element coils 104 will now be explained.

In the MRI apparatus 100, when positions on the top panel 76 are indeterminate, e.g., when the reception coil unit 102 that is disposed to a body surface of the test subject P is present, positions of the element coils 104 included in this reception coil unit 102 are determined as explained below. It is good enough to determine the positions with the reception coil unit 102 alone whose position on the top panel 76 is indeterminate being determined as a target, and the reception coil unit 102 which is of a type fixed to the top panel 76 such as the spinal coil is excluded.

A controller 46 first utilizes a technology disclosed in U.S. Pat. No. 5,936,406 to execute position determining pre-scan. That is, according to the position determining pre-scan, a gradient magnetic field is applied in an alignment direction (the Z-axis direction in FIG. 8) of the element coils 104 in the reception coil unit 102 to obtain projection data in this direction. In this case, the projection data based on magnetic resonance signals 120 received by the element coils 104 placed in the imaging utilization range 106 represents rough positions of the element coils 104 as shown in FIG. 11, for example. Thus, the controller (a calculator) 46 utilizes, e.g., a predetermined threshold value to calculate a central coordinate of the element coils 104. Furthermore, at this time, as a scan parameter, an input unit 44 or the like makes a selection indicative of which element coil 104 in the reception coil 102 is used to perform imaging.

It should be noted that the element coils 104 placed outside the imaging utilization range 106 do not output the magnetic resonance signals or they output small magnetic resonance signals alone. Therefore, the controller 46 ignores output signals from such element coils 104, and calculates a position of each element coil 104 that has output a significant signal.

When ignoring output signals from the element coils 104, projection data based on such signals may not be created, a central coordinate based on the projection data generated from the corresponding signals may not be estimated, or the central coordinate estimated in relation to the element coils 104 that have output the corresponding signals may not be utilized for determination of a position of each element coil 104. Moreover, positions of all the element coils 104 that have output significant signals do not have to be estimated, and positions of some of such element coils 104 alone may be estimated.

The controller 46 displays the thus calculated positions of the element coils 104 on a display unit 42. This dismay may be performed to allow an operator to confirm the positions of the element coils 104 or may be performed to allow the operator to select the element coil 104 that is used for imaging.

Additionally, for example, as shown in FIG. 10, a marker 110 for marking is provided to the bed 18 along a moving direction of the top panel 76. Then, the operator can readily and accurately know a position of the test subject P and positions of the element coils 104 by using this marker 110. Therefore, in this state, as shown in FIG. 2A, imaging using first and second cameras 60a and 60b and audio obtained by an audio recorder 64 are stored.

For example, in the state depicted in FIG. 10, the endmost positioning element coil 104 in the reception coil unit 102-1 is set at a position "7" in the marker 110. Such positional information of the marker 110 is imaged by the first and second cameras 60a and 60b to be recorded, or it is recorded by using the audio recorder 64.

Furthermore, when the marker 110 associated with the endmost positioning element coil 104 cannot be seen for some reason, positional information of the marker 110 associated with the other element coils 104 can be recorded and stored. For instance, in the example depicted in FIG. 10, it can be understood that the element coil 104 that is the third from a head region side of the test subject P is set at a position "9" of the marker 110.

Processing such as imaging, reconstruction, and others after the scan parameter processing is the same as those in the first and second embodiments, thereby omitting an explanation thereof.

As explained above, according to the third embodiment, since a relative position of the patient P and each reception coil is obtained by using data at the time of pre-scan, the same setting of a body position of the patient and each reception coil as that in the previous examination can be configured, thus enabling the same imaging as that in the previous time.

It should be noted that a position of each set element coil 104 is recorded by the camera as position information in association with the marker 110 in this third embodiment, but the present invention is not restricted thereto.

For example, a position of each set element coil 104 may be read by detecting means, e.g., an encoder in association with the maker 110 to be stored as text data in, e.g., a storage unit 40, this data may be read at the time of pre-scan in the next examination, and both the pieces of data may be compared with each other to set a position of each coil.

Further, in the first to third embodiments, as the information to be saved, it is possible to store not only setting information of a body position of the patient and each reception coil but also setting information of, e.g., an ECG sensor.

Furthermore, although the MRI apparatus alone has been explained in the foregoing embodiments, the present invention is not restricted thereto. It is needless to say that the present invention can be applied to any other medical diagnostic imaging apparatus, e.g., an X-ray CT scanner as long as it requires measuring a body position of a patient.

Although the embodiments according to the present invention have been explained, the present invention can be modified in many ways without departing from the scope of the present invention besides the foregoing embodiments.

Moreover, the foregoing embodiments include inventions on various stages, and a variety of inventions can be extracted by appropriately combining a plurality of disclosed constituent requirements. For example, when the problem explained in the section "problems to be solved by the invention" can be solved and the effect described in the section "effect of the invention" can be obtained even though some of all constituent requirements explained in the embodiments are eliminated, a structure from which these constituent elements are eliminated can be extracted as an invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus that receives magnetic resonance signals emitted from a test subject by using a reception coil and reconstructs an image of the test subject from the received magnetic resonance signals, comprising:

a storage unit that stores positions of the test subject and the reception coil when setting the reception coil; and a notification unit that reads and notifies the positions of the test subject and the reception coil stored in the storage unit to confirm the positions of the test subject and the reception coil in a previous time when setting the reception coil for a subsequent time.

2. The apparatus according to claim 1, wherein the storage unit has a recording unit that records positions of the test subject and the reception coil and a storage unit that stores data recorded by the recording unit.

3. The apparatus according to claim 2, wherein the recording unit is formed of an imaging unit that records positions of the test subject and the reception coil as an image, the recording unit records data of the image acquired by the imaging unit, and the notification unit is formed of a display unit that displays an image associated with the data of the image recorded in the recording unit.

4. The apparatus according to claim 2, wherein the recording unit is formed of a recorder that records positions of the test subject and the reception coil in the form of audio and the recording unit records audio data recorded by the recorder, and the notification unit is formed of an audio generation unit that generates audio associated with the audio data recorded in the recording unit.

5. The apparatus according to claim 2, wherein the recording unit has at least one of an imaging unit that records positions of the test subject and the reception coil as an image and a recorder that records the same as audio, the recording unit records at least one of data of the image acquired by the imaging unit and audio data recorded by the recorder, and the notification unit is at least one of a display unit that displays an image associated with the data of the image recorded in the recording unit and an audio generation unit that generates audio associated with the audio data recorded in the same.

6. The apparatus according to claim 1, wherein the storage unit is provided in a server of a medical picture archiving and communication system.

7. A magnetic resonance imaging apparatus that receives magnetic resonance signals emitted from a test subject laid on a bed by using a reception coil in which a plurality of element coils are aligned and reconstructs an image of the test subject from the received magnetic resonance signals, comprising:

a calculation unit that calculates set positions of the plurality of element coils based on each projection data in an alignment direction of the plurality of element coils based on the plurality of magnetic resonance signals received by the plurality of element coils, respectively;

a storage unit that stores positions of the test subject and the plurality of element coils calculated by the calculation unit when setting the plurality of element coils; and a notification unit that reads and notifies the positions of the test subject and the element coils stored in the storage unit to confirm the positions of the test subject and the element coils in a previous time when setting the plurality of element coils for a subsequent time.

8. The apparatus according to claim 7, wherein the storage unit stores positions of the test subject and at least one of the plurality of element coils when setting the plurality of element coils.

9. The apparatus according to claim 7,
wherein the storage unit has a recording unit that records positions of the test subject and the plurality of element coils and a storage unit that stores data recorded by the recording unit.

10. The apparatus according to claim 9,
wherein the recording unit is formed of an imaging unit that records positions of the test subject and the plurality of element coils as an image, the recording unit records data of the image acquired by the imaging unit, and the notification unit is formed of a display unit that displays an image associated with the data of the image recorded in the recording unit.

11. The apparatus according to claim 9,
wherein the recording unit is formed of a recorder that records positions of the test subject and the plurality of element coils as audio and the recording unit records audio data recorded by the recorder, and
the notification unit is formed of an audio generation unit that generates audio associated with the audio data recorded in the recording unit.

12. The apparatus according to claim 9,
wherein the recording unit has at least one of an imaging unit that records positions of the test subject and the plurality of element coils as an image and a recorder that records the same as audio, the recording unit records at least one of data of the image acquired by the imaging unit and audio data recorded by the recorder, and the notification unit is at least one of a display unit that displays an image associated with the data of the image recorded in the recording unit and an audio generation unit that generates audio associated with the audio data recorded in the same.

13. The apparatus according to claim 8, further comprising:
a selection unit that selects an element coil to be used when setting the plurality of element coils,
wherein the storage unit stores positions of the test subject and the element coil selected by the selection unit.

14. The apparatus according to claim 7, further comprising:
a marker that is provided to the bed along a carrying direction of the test subject and indicates set positions of the plurality of element coils,
wherein the storage unit stores set positions of the test subject and the plurality of element coils indicated by the marker when setting the plurality of element coils.

15. The apparatus according to claim 14,
wherein the storage unit has a recording unit that records set positions of the test subject and the plurality of element coils indicated by the marker and a storage unit that stores data recorded by the recording unit.

16. The apparatus according to claim 15,
wherein the recording unit is formed of an imaging unit that records set positions of the test subject and the plurality of element coils indicated by the marker as an image, the recording unit records data of the image acquired by the imaging unit, and the notification unit is formed of a display unit that displays an image associated with the data of the image recorded in the recording unit.

17. The apparatus according to claim 15,
wherein the recording unit is formed of a recorder that records set positions of the test subject and the plurality of element coils indicated by the marker as audio and the recording unit records audio data recorded by the recorder, and
the notification unit is formed of an audio generation unit that generates audio associated with the audio data recorded in the recording unit.

18. The apparatus according to claim 15,
wherein the recording unit has at least one of an imaging unit that records positions of the test subject and the plurality of element coils indicated by the marker as an image and a recorder that records the same as audio, the recording unit records at least one of data of the image acquired by the imaging unit and audio data recorded by the recorder, and the notification unit is at least one of a display unit that displays an image associated with the data of the image recorded in the recording unit and an audio generation unit that generates audio associated with the audio data recorded in the same.

19. The apparatus according to claim 7,
wherein the storage unit is provided in a server of a medical picture archiving and communication system.

20. A position setting support method of a magnetic resonance imaging apparatus that receives magnetic resonance signals emitted from a test subject by using a reception coil and reconstructs an image of the subject from the received magnetic resonance signals, comprising:
previously setting a position of the test subject and positions of the test subject and the reception coil prior to an examination;
recording information indicative of the position of the test subject and the positions of the test subject and the reception coil set at the previously setting;
performing an examination by using the magnetic resonance imaging apparatus;
reading the information indicative of the position of the test subject and the positions of the test subject and the reception coil recorded at the recording before again performing an examination after the examination;
setting a position of the test subject and positions of the test subject and the reception coil at the present time based on the information indicative of the position of the test subject and the positions of the test subject and the reception coil read at the reading the information indicative of the position of the reception coil; and
again performing an examination by using the magnetic resonance imaging apparatus at the position of the test subject and the positions of the test subject and the reception coil set at the setting the positions.

* * * * *